US010550240B2

(12) United States Patent
Tai et al.

(10) Patent No.: US 10,550,240 B2
(45) Date of Patent: Feb. 4, 2020

(54) CARBON MATERIAL-POLYMER STRAIN SENSITIVE FILM AND ITS PREPARATION METHOD

(71) Applicant: University of Electronic Science and Technology of China, Chengdu, Sichuan (CN)

(72) Inventors: Huiling Tai, Sichuan (CN); Xueliang Ye, Sichuan (CN); Zhen Yuan, Sichuan (CN); Rui Guo, Sichuan (CN); Yadong Jiang, Sichuan (CN); Weizhi Li, Sichuan (CN); Xiaosong Du, Sichuan (CN)

(73) Assignee: University of Electronic Science and Technology of China, Chengdu, Sichuan (CN)

(*) Notice: Subject to any disclaimer, the term of this patent is extended or adjusted under 35 U.S.C. 154(b) by 112 days.

(21) Appl. No.: 15/825,109

(22) Filed: Nov. 29, 2017

(65) Prior Publication Data

US 2018/0086893 A1 Mar. 29, 2018

(30) Foreign Application Priority Data

Feb. 13, 2017 (CN) .......................... 2017 1 0076583

(51) Int. Cl.
*B29D 7/01* (2006.01)
*C08J 5/18* (2006.01)
(Continued)

(52) U.S. Cl.
CPC ................ *C08K 3/042* (2017.05); *C08F 2/20* (2013.01); *C08F 26/10* (2013.01); *C08F 120/56* (2013.01);
(Continued)

(58) Field of Classification Search
None
See application file for complete search history.

(56) References Cited

FOREIGN PATENT DOCUMENTS

| | | | |
|---|---|---|---|
| CN | 102786705 A | * | 11/2012 |
| CN | 103663444 A | * | 3/2014 |
| CN | 106119841 A | * | 11/2016 |

OTHER PUBLICATIONS

Lin, W. et al. "Polyaniline/multi-walled carbon nanotube composites for structural vibration damping and strain sensing". J. Mater. Res. 2017, 32(1), 73-83. (Year: 2017).*

* cited by examiner

*Primary Examiner* — Richard A Huhn (57) ABSTRACT

A carbon material-polymer strain sensitive film and its preparation method are disclosed. The carbon material-polymer strain sensitive film includes multiple layers of carbon sensitive films and multiple layers of polymer films, wherein the multiple layers of carbon sensitive films and the multiple layers of polymer films form a multi-layer composite film in sequence through a layer-by-layer assembly process. The preparation method includes steps of: cleaning, processing a hydrophilic treatment and processing a hydrophobic treatment on a rigid substrate in sequence; preparing a carbon material in dispersion solution and a polymer dispersion solution; through a layer-by-layer self-assembly process, growing the polymer and the carbon material in a form of layer-by-layer on the rigid substrate; transferring the composite film from the rigid substrate to a flexible substrate; and pasting two electrodes at two ends of the composite film and encapsulating with a flexible film.

7 Claims, 4 Drawing Sheets

(51) Int. Cl.
*B32B 27/12* (2006.01)
*C08K 3/04* (2006.01)
*C08F 2/20* (2006.01)
*C08F 26/10* (2006.01)
*C08F 120/56* (2006.01)
B32B 27/30 (2006.01)
B32B 27/28 (2006.01)
C08G 73/02 (2006.01)
G01N 21/35 (2014.01)
G01Q 60/24 (2010.01)
H01J 37/28 (2006.01)

(52) U.S. Cl.
CPC ............... *C08K 3/041* (2017.05); *B29D 7/01* (2013.01); *B32B 27/28* (2013.01); *B32B 27/308* (2013.01); *B32B 2250/42* (2013.01); *B32B 2313/04* (2013.01); *B32B 2333/00* (2013.01); *B32B 2355/00* (2013.01); *B32B 2379/00* (2013.01); *C08G 73/0206* (2013.01); *C08J 5/18* (2013.01); *C08L 2203/16* (2013.01); *G01N 2021/3595* (2013.01); *G01Q 60/24* (2013.01); *H01J 37/28* (2013.01)

CARBON MATERIAL-POLYMER STRAIN SENSITIVE FILM AND ITS PREPARATION METHOD

CROSS REFERENCE OF RELATED APPLICATION

The present invention claims priority under 35 U.S.C. 119(a-d) to CN 201710076583.X, filed Feb. 13, 2017.

BACKGROUND OF THE PRESENT INVENTION

Field of Invention

The present invention relates to a preparation method of a carbon material flexible strain sensitive film, and more particularly to a preparation method of a flexible carbon composite strain film through layer-by-layer self-assembly.

Description of Related Arts

Due to high measurement resolution, wide measurement range, immunity from electromagnetic interference, corrosion resistance, impact and vibration resistance, anti-fatigue and long service life, the strain sensor is widely applied to multiple fields such as aerospace, machinery, electricity, chemical industry, construction, medical health and automobile industry. The flexible strain sensor can not only overcome rigidity and brittleness of traditional strain sensors, but also be bent and even wound, thereby greatly expanding applications of the strain sensor in the biomedical field, bionic robot field, intelligent electronic field and material structure defect monitoring field.

Currently, the material, which is made into the flexible strain sensitive film, comprises carbon materials (such as grapheme and carbon tube) and metal materials (such as AuNWs, AgNWs, ZnONWs and Pt), in which due to good conductivity, high specific surface area and excellent mechanical properties, the carbon nanomaterial is widely applied to various functional sensitive film materials. At present, the preparation method of the strain sensitive film comprises chemical vapor deposition, in situ self-assembly, spraying, impregnation and electrospinning. Patent No. CN104257359A discloses a method for preparing a flexible strain sensor based on a carbon material-flexible polymer composite sensitive material, wherein a viscous mixture of the carbon material and the flexible polymer is coated as a sensitive material on the woven fabric to obtain a three-dimensional nanostructure sensitive layer; the preparation method is characterized in that the viscous solution of two kinds of materials is directly mixed with a certain proportion to obtain the viscous mixture; the preparation process is simple and easy to operate, but there are some problems such as poor uniformity of the composite material and poor controllability of the film growth. Patent No. CN103076031A discloses a flexible stretchable strain sensor prepared by electrospinning, in which a prepared conductive polymer spinning solution is injected into a needle tube, and then deposited on a flexible collection substrate through an electrospinning device; the flexible stretchable strain sensor prepared by the above method has good sensitivity and stability, but there are some problems such as high cost and complicated operation. Patent No. CN104406513A discloses a method for preparing a graphene-based surface strain sensor, which comprises steps of spraying graphene oxide onto a substrate, irradiating the graphene oxide with chemical reduction or ultraviolet light, obtaining a graphene film, pasting electrodes on the grapheme film, and then spraying a layer of polymer solution. The strain coefficient of the strain sensor prepared by the above method is five, which is lower than that of the similar strain sensor in the sensitivity, and is poor in the controllability of the preparation process.

SUMMARY OF THE PRESENT INVENTION

Based on the above problems of the flexible strain sensitive film in the preparation process, such as high cost of the film preparation device, complicated operation, poorly controlled preparation process, poor film performance and low practical value, the present invention provides a carbon material-polymer strain sensitive film and its preparation method, for solving poor sensitivity and stability of the single carbon material strain film.

The present invention adopts technical solutions as follows:

A carbon material-polymer strain sensitive film comprises multiple layers of carbon sensitive films and multiple layers of polymer films, wherein the multiple layers of carbon sensitive films and the multiple layers of polymer films form a multi-layer composite film in sequence through a layer-by-layer assembly process.

Preferably, the carbon sensitive films are made from a material which is at least one member selected from a group consisting of graphene, graphene oxide, reduced graphene oxide, graphene quantum dot, graphene nanometer sheet, carbon nanotube, carbon nanofiber, nanometer porous carbon and nano graphite.

The polymer film is made from a material which is soluble in water or alcohol and has a sticky property, and preferably, the material is polyethyleneimine (PEI), polyacrylamide (PAAM) or polyvinylpyrrolidone (PVP).

A preparation method of a carbon material-polymer strain sensitive film comprises steps of:

(1) cleaning, processing a hydrophilic treatment and processing a hydrophobic treatment on a surface of a rigid substrate in sequence;

(2) preparing a carbon material dispersion solution with uniform dispersion and preparing a polymer dispersion solution with uniform dispersion;

(3) after the step (1), sequentially and repeatedly immersing the rigid substrate into the polymer dispersion solution and the carbon material dispersion solution, and preparing a multi-layer composite film on the rigid substrate through a layer-by-layer assembly process;

(4) transferring the multi-layer composite film obtained by the step (3) from the rigid substrate to a flexible substrate; and (5) pasting two electrodes at two ends of the multi-layer composite film and encapsulating with a flexible film.

Preferably, in the step (1), the step of cleaning the surface of the rigid substrate comprises: sequentially ultrasonically cleaning the rigid substrate in acetone, ethanol and deionized water solution for 10-30 min, and then drying under nitrogen;

the step of processing the hydrophilic treatment on the rigid substrate comprises: sequentially putting the cleaned rigid substrate into concentrated sulfuric acid and hydrogen peroxide and respectively ultrasonically cleaning for 15-30 min, and then drying under the nitrogen;

the step of processing the hydrophobic treatment on the rigid substrate comprises: after processing the hydrophilic treatment, putting the rigid substrate into a beaker, dropping TMCS (trimethylchlorosilane) solution into the beaker and sealing an opening of the beaker, and then putting the beaker into a constant temperature water tank, and then water-bathing at 60-80° C. for 40-60 min, and then drying under the nitrogen, so as to transfer the composite film from the rigid substrate to the flexible substrate later, for obtaining a complete flexible composite film.

Preferably, in the step (2), while preparing the carbon material dispersion solution and the polymer dispersion solution, ultrasonic dispersion treatment is supplemented for 20-40 min, and magnetic stirring treatment is performed for 10-20 min.

Preferably, in the step (3), the layer-by-layer assembly process comprises: (A) growing for 2-5 min after immersing the rigid substrate, which is performed the hydrophobic treatment, into the polymer dispersion solution, and taking out the rigid substrate, and then drying through the nitrogen after cleaning through the deionized water solution, and then growing a layer of polymer film on the surface of the rigid substrate; (B) growing for 2-5 min after immersing the rigid substrate with polymer film into the carbon material dispersion solution, and then taking out, and then drying through the nitrogen after cleaning through the deionized water solution, and then growing a layer of carbon sensitive film on the layer of polymer film; and (C) repeating above steps for several times, and finally forming the multi-layer composite film on the rigid substrate.

Preferably, in the step (4), the multi-layer composite thin film is transferred to the flexible substrate through a polymer colloidal material with good adhesion and high melting point, the polymer colloidal material is dimethylsiloxane (PDMS).

Preferably, in the step (5), the electrodes are made from copper, gold, silver, carbon nanotube or graphene, and are drawn through pasting or printing, and the flexible film is made from PDMS (polydimethylsiloxane), polyethylene or polyimide.

In view of the above, beneficially effects of the present invention are as follows:

1. In the present invention, the carbon material and the polymer form a new nanocomposite sensitive material system, which is able to take full advantages of the carbon material such as large specific surface area, excellent mechanical properties and good conductivity, and simultaneously, the polymer is able to greatly improve the adhesion of the carbon material film to the flexible substrate, thus improving the strain recovery performance and stability of the film; furthermore, the polymer is able to effectively improve the dispersion of the carbon material, which is beneficial to the formation of uniform conductive network, so that the sensitivity of a single carbon strain sensitive material is able to be improved.

2. In the present invention, the layer-by-layer self-assembly process is adopted to prepare the strain sensitive film; through the layered alternating deposition method, with the help of intermolecular interaction of every layer (such as electrostatic attraction, hydrogen bond and coordination key), a molecular aggregate or a super-molecular structure with a complete structure, stable performance and a specific function is spontaneously formed between layer and layer. Simultaneously, through adjusting an amount of layers of the self-assembly film, a material thereof and a composite film boundary, best performance parameters of the stain composite film are further preferred. For the above method, the operation process is simple, equipment requirements are low, and the principle is reliable. The prepared sensor has high sensitivity, large strain coefficient, good flexibility, low cost and friendly environment.

3. In the present invention, the rigid substrate is performed hydrophobic treatment to convenient for transferring the composite film from the rigid substrate to the flexible substrate later, so as to obtain the complete flexible composite film. There are two reasons for not directly using the flexible stretchable material. Firstly, a majority of the flexible material substrate in the hydrophilic process will be corroded by concentrated sulfuric acid. Secondly, in the self-assembly process, the flexible substrate is suspended in the solution and unable to be completely impregnated, and is difficult to be controlled in the cleaning process and the drying process.

These and other objectives, features, and advantages of the present invention will become apparent from the following detailed description, the accompanying drawings, and the appended claims.

DETAILED DESCRIPTION OF THE PREFERRED EMBODIMENT

To more clearly understand objectives, technical solutions and advantages, the present invention will be further described in detail with accompanying drawings and embodiments. It should be understood that the specific embodiments described herein are merely illustrative to the present invention and are not intended to limit the present invention.

A carbon material-polymer strain sensitive film comprises multiple layers of carbon sensitive films and multiple layers of polymer films. The carbon sensitive films are made from a material which is at least one member selected from a group consisting of graphene, graphene oxide, reduced graphene oxide, graphene quantum dot, graphene nanometer sheet, carbon nanotube, carbon nanofiber, nanometer porous carbon and nano graphite. The polymer film is made from a material which is soluble in water or alcohol and has a sticky property, and preferably, is polyethyleneimine (PEI), polyacrylamide (PAAM) or polyvinylpyrrolidone (PVP). The multiple layers of carbon sensitive films and the multiple layers of polymer films form a multi-layer composite film through a layer-by-layer assembly process. The multiple layers of carbon sensitive films and the multiple layers of polymer films in the multi-layer composite film are distributed in a form of ". . . - carbon sensitive film-polymer film-carbon sensitive film-polymer film- . . . -carbon sensitive film-polymer film-carbon sensitive film-polymer film- . . . ".

A preparation method of a carbon material-polymer strain sensitive film comprises steps of:

(1) cleaning, processing a hydrophilic treatment and processing a hydrophobic treatment on a surface of a rigid substrate in sequence, wherein:

the step of cleaning the surface of the rigid substrate comprises: sequentially ultrasonically cleaning the rigid substrate in acetone, ethanol and deionized water solution for 10-30 min, and then drying under nitrogen;

the step of processing the hydrophilic treatment on the rigid substrate comprises: sequentially putting the cleaned rigid substrate into concentrated sulfuric acid and hydrogen peroxide and respectively ultrasonically cleaning for 15-30 min, and then drying under the nitrogen;

the step of processing the hydrophobic treatment on the rigid substrate comprises: after processing the hydrophilic treatment, putting the rigid substrate into a beaker, dropping TMCS (trimethylchlorosilane) solution into the beaker and sealing an opening of the beaker, and then putting the beaker into a constant temperature water tank, and then water-bathing at 60-80° C. for 40-60 min, and then drying under the nitrogen;

(2) preparing a carbon material dispersion solution with uniform dispersion and preparing a polymer dispersion solution with uniform dispersion, wherein:

while preparing the carbon material dispersion solution and the polymer dispersion solution, ultrasonic dispersion treatment is supplemented for 20-40 min, and magnetic stirring treatment is performed for 10-20 min; also, the ultrasonic dispersion treatment and the magnetic stirring treatment are alternative;

(3) after the step (1), sequentially and repeatedly immersing the rigid substrate into the polymer dispersion solution and the carbon material dispersion solution, and preparing a multi-layer composite film on the rigid substrate through a layer-by-layer assembly process, wherein:

the layer-by-layer assembly process comprises: (a) growing for 2-5 min after immersing the rigid substrate, which is performed the hydrophobic treatment, into the polymer dispersion solution, and then taking out the rigid substrate, and then drying through the nitrogen after cleaning through the deionized water solution, and then growing a layer of polymer film on the surface of the rigid substrate, (b) growing for 2-5 min after immersing the rigid substrate into the carbon material dispersion solution, and then taking out, and then drying through the nitrogen after cleaning through the deionized water solution, and then growing a layer of carbon sensitive film on the layer of polymer film, and (c) repeating above steps for several times, and finally forming the multi-layer composite film on the rigid substrate;

(4) transferring the multi-layer composite film obtained by the step (3) from the rigid substrate to a flexible substrate, wherein:

the multi-layer composite film is transferred to the flexible substrate through a polymer colloidal material with good adhesion and high melting point, the polymer colloidal material is dimethylsiloxane (PDMS); and (5) pasting two electrodes at two ends of the multi-layer composite film and encapsulating with a flexible film, wherein:

the electrodes are made from copper, gold, silver, carbon nanotube or graphene, and are drawn through pasting or printing, and the flexible film is made from PDMS (polydimethylsiloxane), polyethylene or polyimide.

Preferred Embodiment:

In the preferred embodiment, a graphene-polyethyleneimine composite film is taken as a sensitive layer to prepare a graphene-based flexible strain sensor, which comprises steps of:

(1) selecting glass as a film growth substrate, respectively ultrasonically cleaning the glass through acetone, anhydrous ethanol and deionized water solution for 10-30 min, and then respectively ultrasonically cleaning in sequence through concentrated sulfuric acid, hydrogen peroxide and the deionized water solution for 15-30 min, in such a manner that a semi-hydrophilic semi-hydrophobic surface of the glass is completely hydrophilic, and then drying through nitrogen, and then putting a support stand installed with the completely hydrophilic glass into a clean beaker, dropping an appropriate amount of TMCS (trimethylchlorosilane) solution into the beaker and sealing an opening of the beaker, and then putting the beaker into a constant temperature water tank, and then water-bathing at 65° C. for 40-60 min, and then obtaining a completely hydrophobic glass substrate;

(2) mixing graphene oxide solution with a concentration of 2 mg/ml and a first amount of deionized water with a volume ratio of 1:2-1:3, performing ultrasonic dispersion treatment for 20-40 min, uniformly dispersing the graphene oxide solution, dissolving yellow viscous PEI (polyetherimide) solution in a second amount of deionized water, preparing 1% w/v-5% w/v PEI solution, and then performing ultrasonic dispersion treatment for 20-40 min, and uniformly dispersing the PEI solution;

(3) immersing and growing for 2-3 min after putting the silicalized glass substrate into the 1% w/v-5% w/v PEI solution, taking out and then cleaning with the deionized water solution, and then drying through the nitrogen, and then immersing and growing for 2-3 min after putting the glass substrate into a graphene oxide solution with a concentration of 0.25 mg/ml-1 mg/ml, taking out and then cleaning with the deionized water solution, and then drying through the nitrogen, repeating above steps for several times in sequence, assembling PEI films and graphene oxide films in a form of layer by layer, and finally obtaining a multi-layer composite sensitive film;

(4) weighing polydimethylsiloxane main agent and curing agent with a mass ratio of 10:1, mixing and stirring for 10-20 min till a lot of bubbles are produced, putting a beaker with a mixed solution into a vacuum box, defoaming at −0.05 MPa-0.01 MPa for 10-20 min, obtaining PDMS (dimethylsiloxane) precursor fluid, coating the PDMS precursor fluid on the glass substrate with the multi-layer composite sensitive film through a spinning method, respectively adjusting a rotating speed and a rotating time of a spinner to be in a range of 500 rmp-800 rmp and 9 s-30 s, obtaining a flexible substrate with different thicknesses, putting the glass substrate coated with the PDMS through the spinning method into a vacuum drying oven, baking at 60-70° C. for 40-60 min, taking out the glass substrate, mechanically peeling the PDMS off the glass substrate, transferring the composite film to the PDMS, and obtaining a flexible composite film; and (5) putting the flexible composite film into an atmosphere furnace, annealing at 220° C. for 2 h, deoxygenizing the graphene oxide into the graphene, plating copper lines as electrodes on a surface of the graphene-based flexible composite film through conductive silver paste, encapsulating and obtaining the graphene-based flexible strain sensor.

The present invention tests the strain-sensitive properties of the prepared flexible composite film. Accordingly, the results show that the resistance of the flexible composite film changes with the change of the bending or the degree of stretching, the repeatability is good, the response is high, the sensitivity is high, and the resistance of the flexible composite film is still large in strain coefficient under a small strain.

Figure 1:
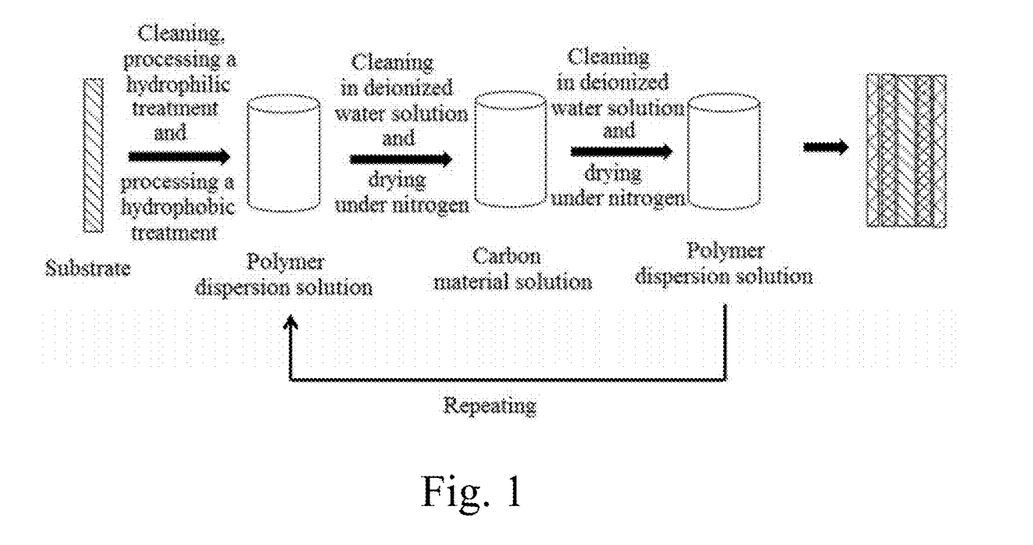
FIG. 1 is a flow chart of a layer-by-layer assembly process provided by the present invention.
Figure 2:
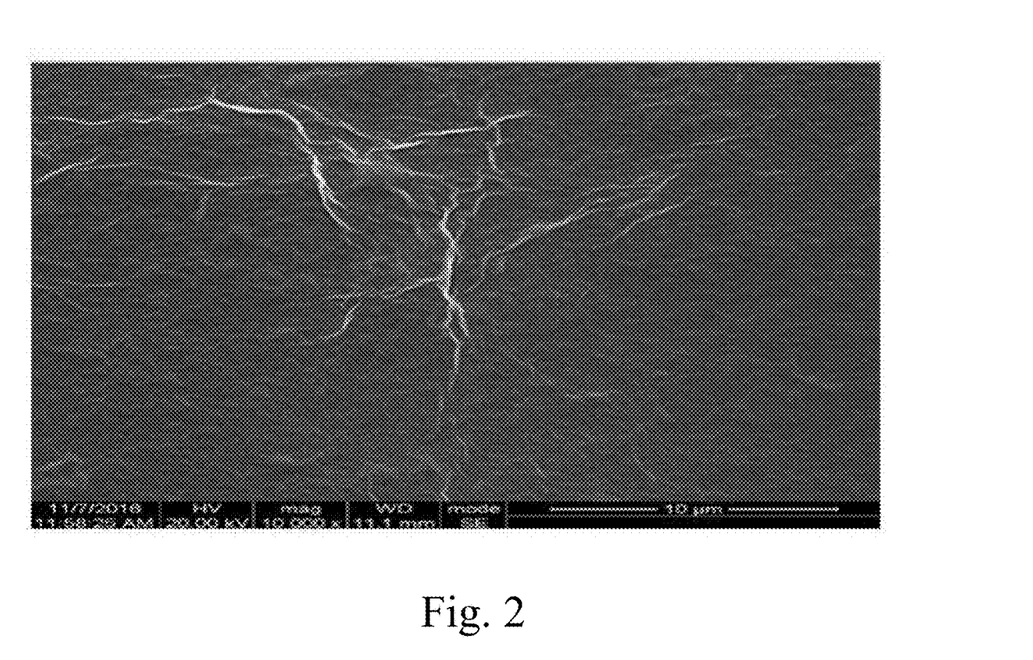
FIG. 2 is a SEM (scanning electron microscopy) of a graphene-based composite film provided by the present invention.
Figure 3:
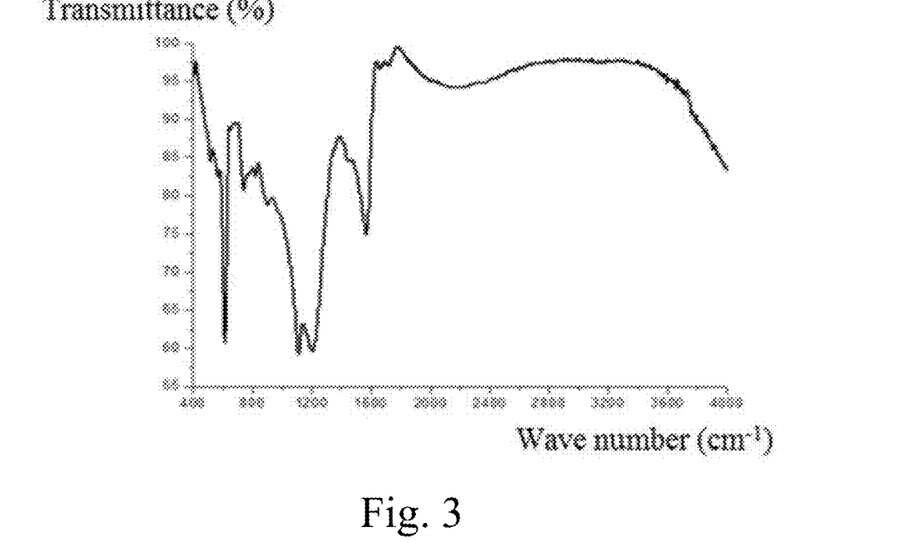
FIG. 3 is a Fourier transform infrared spectroscopy of the graphene-based composite film provided by the present invention.
Figure 4:
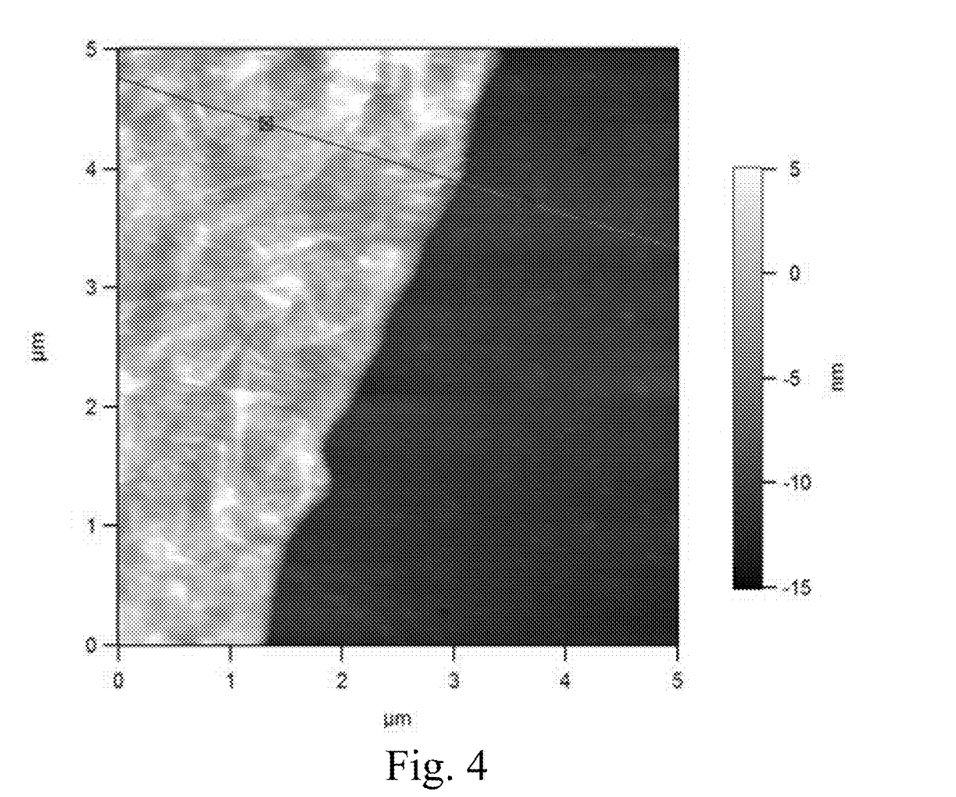
FIG. 4 is an AFM (atomic force microscopy) diagram at faults of the graphene-based composite film provided by the present invention.
Figure 5:
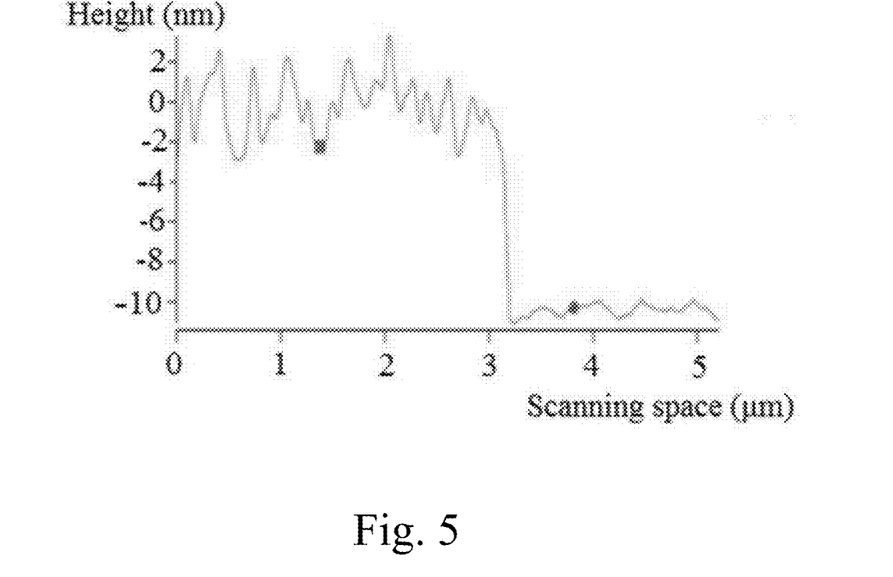
FIG. 5 is a thickness variation diagram of the graphene-based composite film provided by the present invention.

FIG. 1 shows a flow chart of a preparation method of a multi-layer composite film through a layer-by-layer assembly process. FIG. 2 shows a surface morphology of the composite film, wherein the composite film is corrugated. FIG. 3 shows an Fourier infrared absorption spectroscopy of the composite film, and it can be seen that the absorption peak of the —OH functional group near 3385 $cm^{-1}$ disappears obviously, the absorption peak of the C—OH functional group near 1314 $cm^{-1}$ and 1413 $cm^{-1}$ disappears obviously, which indicates that graphene is fully deoxygenized. FIG. 4 is an AFM sectional view of a self-assembled two-layer graphene composite film, wherein the white area is the composite film, the black area is the substrate, which can be seen that the sensitive film is successfully transferred from the glass substrate to the PDMS flexible substrate, a thickness of a single layer composite film is calculated to be 4 nm, as shown in FIG. 5.

In this embodiment, two ends of the encapsulated graphene-based flexible strain sensor are fixed, and a dynamic strain test platform is used to set parameters of the moving platform and stretch the strain sensor. The resistance of the graphene-based flexible strain sensor varies abruptly with the stretching of the film, and the resistance value is collected by a keithley 2700 signal collector. Strain sizes and resistance response curves are tested for real-time monitoring human physiological parameters (such as blood pressure, heart rate and pulse) and movement status (such as finger knee activity).

Figure 6:
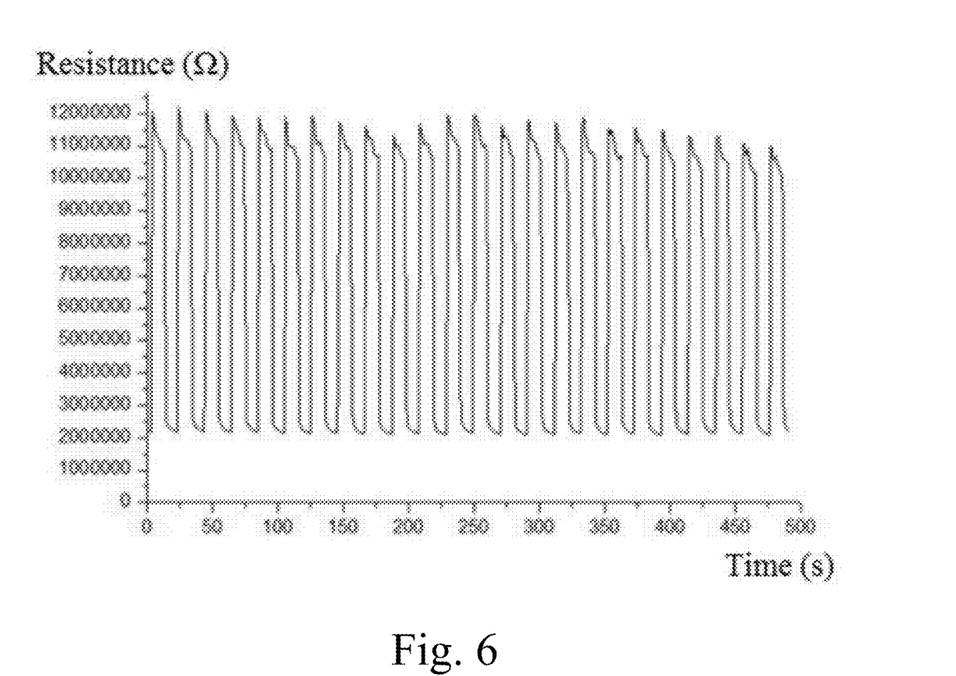
FIG. 6 is a response curve of a graphene-based flexible strain sensor provided by the present invention.
Figure 7:
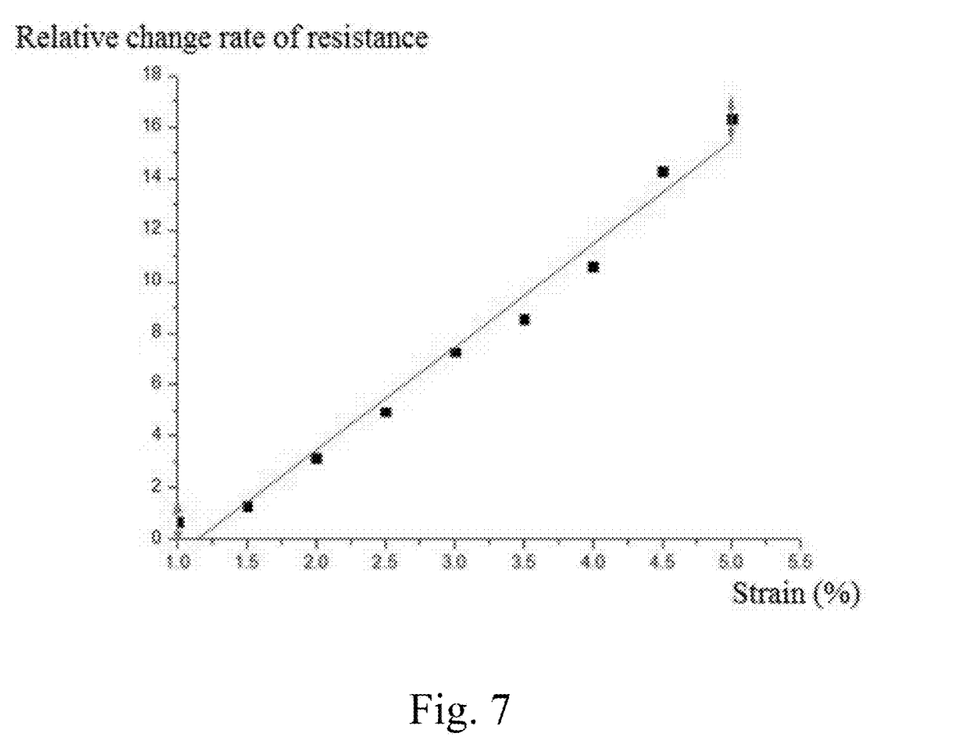
FIG. 7 shows the variation relationship of the relative change rate of the resistance of the to graphene-based composite film under different strains.
Figure 8:
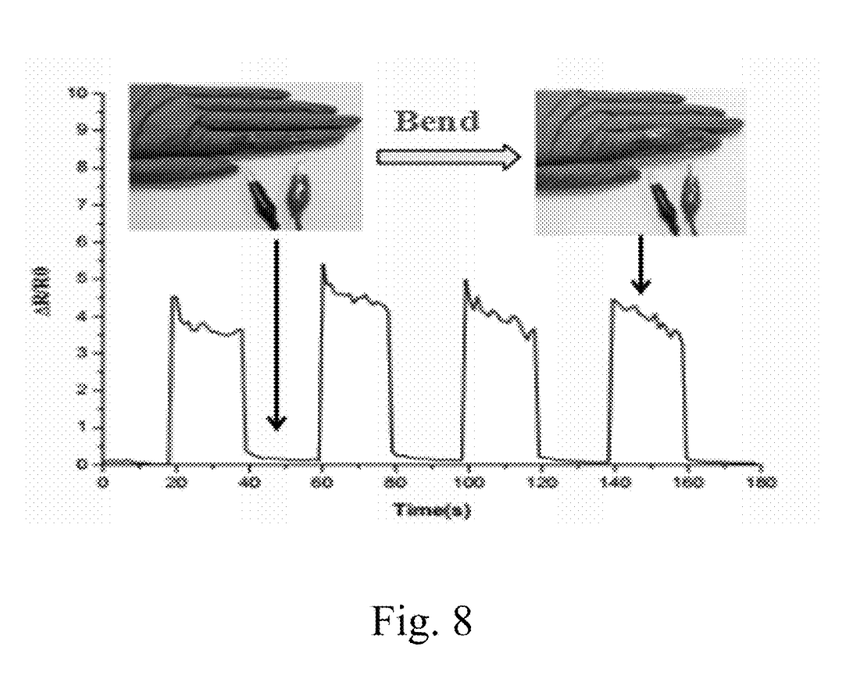
FIG. 8 shows the variation curve of the relative resistance change rate of the finger before and after being weakly bent.

The present invention utilizes the dynamic test platform to apply a tensile force at both ends of the film to deform, for holding and stretching the deformed graphene composite film strain sheet for 10 s, followed by the dynamic platform moves to in situ to release the tensile deformation for 10 s, so that the film is restored to an original state. Therefore, 20 s is a test cycle, and the test is repeated for dozens of cycles. As shown in FIG. 6, it can be obviously seen that when the graphene composite film is stretched and deformed, the resistance is increased dramatically, indicating that the sensor has high sensitivity and high stability for the stretch strain. FIG. 7 shows the variation relationship of the relative change rate ($\Delta R/R_0$) of the resistance of the graphene-based composite film under different tensile strains. It can be seen from FIG. 7 that when the tensile deformation of the film increases, the resistance increases, and the relative resistance change rate is linear with the strain size. In this embodiment, the prepared flexible strain sensitive film is able to be adapted for monitoring the movement of the human body. FIG. 8 shows the variation curve of the relative resistance change rate of the finger before and after being weakly bent. It can be seen from FIG. 8 that the composite film has good response and stability, and is able to be applied to real-time monitoring of human motion.

The foregoing is merely illustrative to the preferred embodiment of the present invention and is not intended to limit the present invention, and any modifications, equivalent substitutions and improvements within the spirit and principles of the present to invention are intended to be encompassed by the present invention.

What is claimed is:

1. A carbon material-polymer strain sensitive film comprising: multiple layers of carbon films and multiple layers of polymer films, wherein: the multiple layers of carbon films and multiple layers of polymer films form a multi-layer composite film in sequence through a layer-by-layer assembly process;
   the polymer films are made from a material which is soluble in water or alcohol; and
   the polymer films are made from polyethyleneimine (PEI), polyacrylamide (PAAM), or polyvinylpyrrolidone (PVP).

2. A preparation method of a carbon material-polymer strain sensitive film comprising steps of:
   (1) cleaning, processing a hydrophilic treatment and processing a hydrophobic treatment on a surface of a rigid substrate in sequence;
   (2) preparing a carbon material dispersion solution with uniform dispersion and preparing a polymer dispersion solution with uniform dispersion;
   (3) after the step (1), sequentially and repeatedly immersing the rigid substrate into the polymer dispersion solution and the carbon material dispersion solution, and preparing a multi-layer composite film on the rigid substrate through a layer-by-layer assembly process;
   (4) transferring the multi-layer composite film obtained by the step (3) from the rigid substrate to a flexible substrate; and
   (5) pasting two electrodes at two ends of the multi-layer composite film and encapsulating with a flexible film.

3. The preparation method of the carbon material-polymer strain sensitive film, as recited in claim 2, wherein:
   in the step (1), the step of cleaning the surface of the rigid substrate comprises: sequentially ultrasonically cleaning the rigid substrate in acetone, ethanol and deionized water solution for 10-30 min, and then drying under nitrogen;
   the step of processing the hydrophilic treatment on the rigid substrate comprises: sequentially putting the cleaned rigid substrate into concentrated sulfuric acid and hydrogen peroxide and respectively ultrasonically cleaning for 15-30 min and then drying under the nitrogen;
   the step of processing the hydrophobic treatment on the rigid substrate comprises: after processing the hydrophilic treatment, putting the rigid substrate into a beaker, dropping TMCS (trimethylchlorosilane) solution into the beaker and sealing an opening of the beaker, and then putting the beaker into a constant temperature water tank, and then water-bathing at 60-80° C. for 40-60 min, and then drying under the nitrogen.

4. The preparation method of the carbon material-polymer strain sensitive film, as recited in claim 2, wherein: the step (2) further comprises performing ultrasonic dispersion for 20-40 min, and magnetic stirring treatment for 10-20 min.

5. The preparation method of the carbon material-polymer strain sensitive film, as recited in claim 2, wherein: in the step (3), the layer-by-layer assembly process comprises: (A) growing for 2-5 min after immersing the rigid substrate, which is performed the hydrophobic treatment, into the polymer dispersion solution, and then taking out the rigid substrate, and then drying through the nitrogen after cleaning through the deionized water solution, and then growing a layer of polymer film on the surface of the rigid substrate, (B) growing for 2-5 min after immersing the rigid substrate into the carbon material dispersion solution, and then taking out, and then drying through the nitrogen after cleaning through the deionized water solution, and then growing a layer of carbon sensitive film on the layer of polymer film, and (C) repeating above steps for several times, and finally forming the multi-layer composite film on the rigid substrate.

6. The preparation method of the carbon material-polymer strain sensitive film, as recited in claim 2, wherein: in the step (4), the multi-layer composite film is transferred to the flexible substrate through a polymer colloidal material with good adhesion and high melting point.

7. The preparation method of the carbon material-polymer strain sensitive film, as recited in claim 2, wherein: in the step (5), the electrodes are made from copper, gold, silver, carbon nanotube or graphene, and are drawn through pasting or printing, and the flexible film is made from PDMS (polydimethylsiloxane), polyethylene or polyimide.

* * * * *